United States Patent [19]
Erlanson

[11] Patent Number: 6,143,776
[45] Date of Patent: Nov. 7, 2000

[54] TOSYLPROLINE ANALOGS AS THYMIDYLATE SYNTHASE INHIBITORS

[75] Inventor: Daniel A. Erlanson, San Francisco, Calif.

[73] Assignee: Sunesis Pharmaceuticals, Inc., Redwood City, Calif.

[21] Appl. No.: 09/496,378

[22] Filed: Feb. 2, 2000

[51] Int. Cl.[7] .......................... A61K 31/401; A61P 31/00; A61P 35/00; C07D 207/48
[52] U.S. Cl. ............................. 514/424; 514/75; 514/91; 514/142; 514/359; 514/381; 514/382; 514/425; 514/428; 514/538; 514/541; 514/542; 514/603; 514/608; 514/617; 514/620; 514/646; 514/784; 548/253; 548/254; 548/255; 548/542; 548/547; 560/429; 560/430; 560/433; 560/442; 562/11; 562/14; 562/15; 562/16; 562/30; 562/44; 564/163
[58] Field of Search ..................................... 548/542, 547; 514/424, 425, 428

[56] References Cited

U.S. PATENT DOCUMENTS

| | | | |
|---|---|---|---|
| 4,992,550 | 2/1991 | Hughes | 544/284 |
| 5,561,133 | 10/1996 | Bisset et al. | 514/259 |
| 5,955,463 | 9/1999 | Pegg et al. | 514/259 |

FOREIGN PATENT DOCUMENTS 2 065 653 B  3/1983  United Kingdom .

OTHER PUBLICATIONS

Takimoto, "Antifolates in Clinical Development", *Seminars in Oncology*, 24(5), Supp. 18, S18–40—S18–51 (1997).

Marsham et al., "Design and Synthesis of Potent Non–Polyglutamatable Quinazoline Antifolate Thymidylate Synthase Inhibitors", *J. Med. Chem.*, 42, 3809–3820 (1999).

Cunningham et al., "Tomudex' (ZD 1694): Results of a Randomied Trial in Advanced Coloreactal Cancer Demonstrate Efficacy and Reduced Mucositis and Leucopenia", *Eur. J. Cancer*, 31A(12), 1945–1954 (1995).

Jackman et al., "The Antitumour Activity of ZD9331, a Non–polyglutamatable Quinazoline Thymidylate Synthase Inhibitor", pp. 185–188 in Purine and Pyrimidine Metabolism in Man VIII, ed. Sahota and Taylor, Plenum Press, New York (1995).

Wahba et al., "Direct Spectrophotometric Evidence for the Oxidation of Tetrahydrofolate During the Enzymatic Synthesis of Thymidylate", *J. Biol. Chem.*, 236(3). PC11–PC12 (1961).

Chen et al., "Inhibition of Thymidylate Synthase by Pyridoxal Phosphate", *Int. J. Biochem.*, 21(11), 1217–1221 (1989).

Lippmann et al., "The Effect of Estrogens and Antiestrogens on Hormone–responsive Human Breast Cancer in Long–Term Tissue Culture", *Cancer Res.*, 36, 4595–4601 (1976).

Fischer et al., "I. Development, Maintenance and Assay of Drug Resistance", *Meth. Med. Res.*, 10, 247–262 (1964).

*Primary Examiner*—Cecilia Tsang
*Assistant Examiner*—Jane C. Oswecki
*Attorney, Agent, or Firm*—Heller Ehrman White & McAuliffe LLP

[57] ABSTRACT

Tosylproline analogs of formula I, methods of making them, pharmaceutical compositions containing them, and methods for their use. The compounds are thymidylate synthase inhibitors; and are useful as anti-tumor agents and as anti-parasitics, anti-bacterials, anti-fungals, and anti-virals.

20 Claims, No Drawings

TOSYLPROLINE ANALOGS AS THYMIDYLATE SYNTHASE INHIBITORS

BACKGROUND OF THE INVENTION

1. Field of the Invention

This invention relates to thymidylate synthase (TS) inhibitors. In particular, this invention relates to certain tosylproline analogs that are TS inhibitors, to methods of making them, to pharmaceutical compositions containing them, and to their uses.

2. Description of Related Art

Thymidylate synthase is an essential enzyme for virtually all living organisms. Together, TS, dihydrofolate reductase (DHFR), and serine hydroxymethylase form a biochemical functional unit, the thymidylate synthase cycle, that provides the sole de novo pathway for synthesis of the DNA base thymidine 5'-monophosphate (dTMP) from the RNA base uridine 5'-monophosphate (dUMP). Thus, TS and DHFR are both targets for anti-cancer drug development. Because TS is essential for all living species, and the TS gene is even found in many viruses, it is also a target for development of anti-parasitic, anti-bacterial, anti-fungal, and anti-viral agents.

TS is an especially attractive drug target for the following reasons: (i) it is the only enzyme in the cell in which 5,10-methylenetetrahydiofolate (mTHF) is oxidized during one-carbon transfer, and thus the associated binding site is unique; (ii) it is the rate-limiting step in the thymidylate synthase cycle; (iii) the TS gene is not as prone to amplification as is the DHFR gene, and therefore resistance by this mechanism should be less frequent; (iv) inhibition of either TS or DHFR causes 'thymineless death' of the cell, but TS inhibitors do not cause purine depletion and the concomitant side-effects in normal human cells, as do DHFR inhibitors; and (v) tumor cells are especially sensitive to TS inhibition because the activity of TS is unusually high in rapidly proliferating cells, while this activity is barely detectable in non-proliferating cells: the levels of mRNA for TS increase up to 1000-fold higher in relation to DHFR in certain tumor cells, presumably to support the increased requirement for dTMP in rapidly dividing cells.

Since its discovery in 1957, 5-fluorouracil (5-FU), a prodrug that targets TS, has been used in the USA as a principal drug in chemotherapy aimed at cancers of internal organs. 5-FU enters the cell, becomes ribosylated and phosphorylated, and forms a covalent ternary complex with TS and mTHF. However, 5-FU has serious adverse side-effects because it affects at least seven other recognized biochemical pathways, and also becomes incorporated into DNA. See Takimoto C: Antifolates in clinical development. Semin Oncol (Supp 18):S18–40-S18–51, 1987, and references cited therein for the structures and properties of the compounds discussed in this section.

LY 231514 is a classical antifolate originally thought to be a pure TS inhibitor but later recognized to inhibit purine synthesis and DHFR activity. It must be polyglutamated by folylpolyglutamyl synthase for activity. LY 231514 has been studied in a number of clinical trials, with activity noted in non-small cell lung cancer, breast cancer, and colorectal cancer, at doses typically around 500–600 mg/m$^2$ in a ten-minute IV infusion every three weeks.

Raltritrexed is a pure TS inhibitor that has been approved for use in Europe for metastatic colorectal cancer and is currently in Phase III testing in the USA. It must also be polyglutamated for activity. Raltritrexed has been reported to be active in colorectal cancer, breast cancer, ovarian cancer, and non-small cell lung cancer, with similar anti-tumor response rates and lower toxicity than 5-FU/-leucovorin. A typical dose is 3 mg/m$^2$ in a fifteen-minute IV infusion every three weeks. See U.S. Pat. No. 4,992,550; Marsham P R, Wardleworth J M, Boyle F T, et al: Design and synthesis of potent non-polyglutamatable quinazoline antifolate thymidylate synthase inhibitors. J Med Chem: 42:3809–3820, 1999; and Cunningham D, Zalcberg J R, Rath U, et al: 'Tomudex' (ZD1694): Results of a randomized trial in advanced colorectal cancer demonstrate efficacy and reduced mucositis and leucopenia. Eur J Cancer: 31A: 1945–1954, 1995.

ZD 9331, a derivative of raltritrexed, is a water-soluble pure TS inhibitor that is not polyglutamated within the cell. It is a more potent TS inhibitor than raltritrexed polyglutamates, and is presently undergoing Phase II trials. See U.S. Pat. No. 5,955,463; and Jackman A L, Kimbell R, Brown M, et al: The anti-tumor activity of ZD 9331, a non-polyglutamatable quinazoline thymidylate synthase inhibitor. In Purine and Pyrimidine Metabolism in Man VIII (ed. Sahota A and Taylor M) 185–188, Plenum Press, N.Y., 1995.

The disclosures of these and other documents referred to throughout this application are incorporated herein by reference.

Thus TS inhibitors are well-established as anti-tumor agents, especially for solid tumors.

Immunocompromised individuals, e.g. patients with HIV/AIDS, show opportunistic infections with fungi, with bacteria such as *Pneumocystis carinii* and *Mycobacterium tuberculosis*, and with other pathogens that can typically reduce life expectancy, often by many years. Other infections, e.g. parasitic infections, affect a significant proportion of the world's population. TS inhibitors with 100-fold selectivity for bacterial TS over human TS have been discovered, indicating that screening of compounds active against TS may lead to broad applications for TS inhibitors outside of cancer treatment, such as for anti-parasitic, anti-bacterial, anti-fungal, and anti-viral agents; and TS has been isolated and purified from a number of these organisms. TS from at least the following organisms is available: *Pneumocystis carinii* pneumonia is the most common lethal infection of AIDS patients. TS is the first protein that has been isolated and purified from *Pneumocystis carinii*. Tuberculosis has undergone a marked increase in the USA, among both HIV-negative and, especially, HIV-positive individuals. Multi-drug resistant forms of *Mycobacterium tuberculosis* are rapidly emerging. *Toxoplasma gondii* is an opportunistic pathogen frequently infecting immunocompromised individuals. Current therapies have serious side-effects. *Plasmodium falciparum* is the protozoan responsible for most cases of human malaria. There are strains resistant to most of the common anti-malarial drugs; and mefloquine, the most recent drug, has been recognized as a drug possibly inducing psychosis. *Trypanosoma cruzi* causes Chagas' disease. There is currently no satisfactory treatment. *Leishmania major* causes leishmaniasis, a disease affecting persons in the Mediterranean, Middle East, India, and China. Current therapy involves the use of toxic antimony compounds. *Cryptococcus neoformans* infection is frequently associated with AIDS. *Cryptosporidium parvum* causes chronic anti-microbial resistant gastrointestinal infections in immuno-compromised individuals. In addition, as mentioned before, many viruses carry the TS gene in their DNA.

Thus TS inhibitors may prove valuable as anti-parasitics, anti-bacterials, anti-fungals, and anti-virals.

SUMMARY OF THE INVENTION

In a first aspect, this invention provides compounds of formula I:

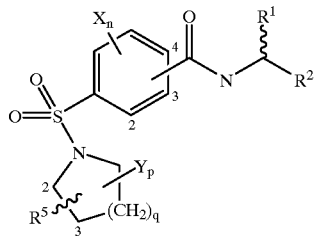

(I)

where:
R¹ is —COOH, —CONH₂, —SO₃H, —SO₂NH₂, —PO₃H₂;
R² is $C_{1-6}$ alkyl optionally substituted with —COOH, —CONH₂, —CONHR³, —CONHCOR⁴, —CONHSO₂R⁴, —SO₃H, —SO₂NH₂, —SO₂NHR³, —SO₂NHCOR⁴, —SO₂NHSO₂R⁴, —PO₃H₂, —4-(1,2,3-triazolyl), —5-tetrazolyl, —5-(3-oxo-1,2,4-triazolyl), —S(O)$_m$-4-(1,2,3-triazolyl), —S(O)$_m$-5-tetrazolyl, or —S(O)$_m$-5-(3-oxo-1,2,4-triazolyl);
R³ is a group such that R³—NH₂ is an amino acid;
R⁴ is $C_{1-4}$ alkyl, trifluoromethyl, or phenyl optionally substituted with methyl, trifluoromethyl, or nitro;
m is 0, 1, or 2;
each X and Y, which may be the same or different, is independently selected from methyl, ethyl, isopropyl, ethenyl, ethynyl, fluoro, chloro, bromo, methylthio, hydroxy, methoxy, carboxy, and methoxycarbonyl;
n is 0, 1, 2, or 3;
p is 0, 1, or 2;
q is 1 or 2;
R⁵ is —COOH, —CONH₂, —CONHR², —SO₃H, —SO₂NH₂, —SO₂NHR², or —PO₃H₂, and the pharmaceutically acceptable salts and esters thereof.

In a second aspect, this invention provides pharmaceutical compositions comprising a pharmaceutically acceptable excipient and a therapeutically effective amount of at least one compound of this invention. These compositions find use as anti-tumor, anti-parasitic, anti-bacterial, anti-fungal, and anti-viral agents.

In a third aspect, this invention provides a method of treating an animal having a disease capable of treatment by administration of a thymidylate synthase inhibitor, comprising administration to that animal of a therapeutically effective amount of at least one compound of this invention, optionally in conjunction with at least one other conventional therapeutic agent for the disease being treated.

In a fourth aspect, this invention provides methods of preparing the compounds of the first aspect of this invention.

DETAILED DESCRIPTION OF THE PREFERRED EMBODIMENTS

Definitions

"Alkyl" means a linear hydrocarbyl group having from one to the number of carbon atoms specified, or a branched or cyclic hydrocarbyl group having from three to the number of carbon atoms specified. Exemplary alkyl groups include methyl, ethyl, isopropyl, cyclopropyl, tert-butyl, cyclopropylmethyl, and hexyl.

"Animal" includes humans and non-human mammals, such as companion animals (cats, dogs, and the like) and farm animals (cattle, horses, sheep, goats, swine, and the like).

"Disease" includes any unhealthy condition of an animal, including particularly tumors, especially tumors of the internal organs, and parasitic, bacterial, fungal, and viral infections.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The compound of this invention possess one or more chiral centers, and can therefore be produced as individual stereoisomers or as mixtures of stereoisomers, depending on whether individual stereoisomers or mixtures of stereoisomers of the starting materials are used. Unless indicated otherwise, the description or naming of a compound or group of compounds is intended to include both the individual stereoisomers or mixtures (racemic or otherwise) of stereoisomers. Methods for the determination of stereochemistry and the separation of stereoisomers are well known to a person of ordinary skill in the art [see the discussion in Chapter 4 of March J: Advanced Organic Chemistry, 4th ed. John Wiley and Sons, New York, N.Y., 1992].

Implicit hydrogen atoms (such as the hydrogen on the benzamide nitrogen, hydrogens on the benzene, etc.) are omitted from the formulae for clarity, but should be understood to be present.

Presently Preferred Compounds

While the broadest definition of the invention is set out in the Summary of the Invention, certain compounds of this invention are presently preferred.

Presently preferred compounds of this invention are compounds of formula I where:

the —CONHCHR$^1$R$^2$ group is at the 3- or 4-position, especially the 4-position;

R$^1$ is —COOH;

R$^2$ is C$_{2-6}$ alkyl;

the substituent on R$^2$ is present and is —COOH, —CONH$_2$, —CONHR$^3$, —SO$_3$H, —SO$_2$NH$_2$, —SO$_2$NHR$^3$, —PO$_3$H$_2$, —4-triazolyl, —5-tetrazolyl, —5-(3-oxo-1,2,4-triazolyl), —S(O)$_m$-4-triazolyl, —S(O)$_m$-5-tetrazolyl, or —S(O)$_m$-5-(3-oxo-1,2,4-triazolyl), especially —COOH, —CONH$_2$, —CONHR$^3$, —SO$_2$NH$_2$, —SO$_2$NHR$^3$, -4-triazolyl, -5-tetrazolyl, or -5-(3-oxo-1,2,4-triazolyl), particularly —CONHR$^3$ and —SO$_2$NHR$^3$;

the substituent on R$^2$ is at the ω-position of R$^2$ (i.e. the position furthest from the benzene ring);

R$^3$ is such that R$^3$—NH$_2$ is an acidic amino acid such as aspartic acid, aspartamine, glutamic acid, glutamine, 2-aminohexanedioic acid, 2-aminoheptanedioic acid, 2-aminooctanedioic acid, or polyglutamic acid, especially glutamic acid, 2-aminohexanedioic acid, 2-aminoheptanedioic acid, or 2-aminooctanedioic acid;

R$^4$ is C$_{1-4}$ alkyl;

each X and Y, which may be the same or different, is methyl, ethyl, fluoro, chloro, bromo, methoxy, carboxy, or methoxycarbonyl, especially methyl, fluoro, chloro, or bromo;

n is 0 or 1;

p is 0 or 1;

the R$^5$ group is at the 2- or 3-position; and

R$^5$ is —COOH, —CONHR$^{2'}$, —SO$_3$H, or —SO$_2$NHR$^{2'}$, or —PO$_3$H$_2$, especially —CONHR$^{2'}$ or —SO$_2$NHR$^{2'}$, where R$^{2'}$ is C$_{2-6}$ alkyl, the substituent on R$^{2'}$ is present and is —COOH, —CONH$_2$, —SO$_3$H, —SO$_2$NH$_2$, -4-triazolyl, -5-tetrazolyl, -5-(3-oxo-1,2,4-triazolyl), -S(O)$_m$-4-triazolyl, -S(O)$_m$-5-tetrazolyl, or —S(O)$_m$-5-(3-oxo-1,2,4-triazolyl), especially where the substituent is —COOH, and the substituent is at the ω-position of R$^{2'}$ (i.e. the position furthest from the ring);

and their individual stereoisomers, and the pharmaceutically acceptable salts and esters thereof.

A number of different preferences have been given above, and following any one of these preferences results in a compound of this invention that is more presently preferred than a compound in which that particular preference is not followed. However, these preferences are generally independent [although some (alternative) preferences are mutually exclusive], and additive; and following more than one of these preferences may result in a more presently preferred compound than one in which fewer of the preferences are followed.

Presently preferred classes of compounds of this invention include those where:

(a) R$^1$ is —COOH; R$^2$ is C$_{2-6}$ alkyl ω-substituted with —COOH, —CONH$_2$, —CONHR$^3$, —SO$_2$NH$_2$, or —SO$_2$NHR$^3$, -4-triazolyl, or -5-tetrazolyl; R$^3$ is an acidic amino acid; each X and Y is independently methyl, ethyl, fluoro, chloro, bromo, methoxy, carboxy, or methoxycarbonyl; n and p are independently 0 or 1; and R$^5$ is —CONHR$^{2'}$ where R$^{2'}$ is C$_{2-6}$ alkyl ω-substituted with —COOH, —CONH$_2$, —SO$_3$H, —SO$_2$NH$_2$, -4-triazolyl, or -5-tetrazolyl;

(b) R$^1$ is —COOH; R$^2$ is C$_{2-6}$ alkyl ω-substituted with —CONHR$^3$ or —SO$_2$NHR$^3$; R$^3$ is an acidic amino acid; each X and Y is independently methyl, ethyl, fluoro, chloro, bromo, or methoxy; n and p are independently 0 or 1; and R$^5$ is —CONHR$^{2'}$ where R$^{2'}$ is C$_{2-6}$ alkyl ω-substituted with —COOH, —CONH$_2$, -4-triazolyl, or -5-tetrazolyl;

(c) R$^1$ is —COOH; R$^2$ is C$_{2-6}$ alkyl ω-substituted with —CONHR$^3$; R$^3$ is an acidic amino acid selected from glutamic acid, 2-aminohexanedioic acid, 2-aminoheptanedioic acid, or 2-aminooctanedioic acid; n and p are 0; and R$^5$ is —CONHR$^{2'}$ where R$^{2'}$ is C$_{2-6}$ alkyl ω-substituted with —COOH or —CONH$_2$;

(d) R$^1$ is —COOH; R$^2$ is C$_{2-6}$ alkyl ω-substituted with —COOH; n and p are 0; and R$^5$ is —CONHR$^{2'}$ where R$^{2'}$ is C$_{2-6}$ alkyl ω-substituted with —COOH or —CONH$_2$;

and their individual stereoisomers, and the pharmaceutically acceptable salts and esters thereof.

Presently preferred compounds of this invention include:

2-[4-(2-carboxypyrrolidine-1-sulfonyl)benzoylamino] octanedioic acid;

2-[4-(2-carboxypyrrolidine-1-sulfonyl)benzoylamino]-4-[1,3-dicarboxypropylaminocarbonyl]butanoic acid [a compound having a glutamylglutamic acid side chain];

2-[4-(2-carboxypiperidine-1-sulfonyl)benzoylamino]-4-[1,3-dicarboxypropylaminocarbonyl]butanoic acid;

2-{4-[2-(2-carboxyethylaminocarbonyl)pyrrolidine-1-sulfonyl]benzoylamino}pentanedioic acid [the compound of Example 2];

2-{4-[2-(3 -carboxypropylaminocarbonyl)-pyrrolidine-1-sulfonyl]benzoylamino}pentanedioic acid;

2-{4-[2-(5-carboxypentylaminocarbonyl)-pyrrolidine-1-sulfonyl]benzoylamino}pentanedioic acid;

2-{4-[2-(3-methylbutylaminocarbonyl)-pyrrolidine-1-sulfonyl]benzoylamino}pentanedioic acid;

and their individual stereoisomers, and the pharmaceutically acceptable salts and esters thereof.

Pharmacology and Utility

The compounds of this invention are thymidylate synthase inhibitors. Their activity as TS inhibitors in vivo can be measured directly by measurement of the inhibition of TS (especially thymidylate synthase associated with tumor cell lines), by methods such as those discussed in Wahba A J and Friedkin M: Direct spectrophotometric evidence for the oxidation of tetrahydrofolate during the enzymatic synthesis of thymidylate. J Biol Chem: 236: PC11–PC12, 1961; and Chen S C, Daron H H, and Aull J L: Inhibition of thymidylate synthase by pyridoxal phosphate. Int J Biochem: 21: 1217–1221, 1989; and as discussed in Example 3. Their activity can also be measured in vitro by measurement of the inhibition of growth of certain tumor cell lines, such as mouse L1210 and human W1L2 cells, and by measuring the affinity of the compounds for the reduced folate/methotrexate cell membrane carrier, as discussed in Jackman et al., mentioned previously, and the references cited therein, and in UK Patent Specification No. 2065653B; and the MFC-7 human breast cancer cell line [see Lippman et al.: Cancer Res: 36: 4595, 1976]. Their activity can be measured in vivo by activity against experimental tumors (murine and human xenografts) in mice, also as discussed in Jackman et al. and the references cited therein. Their activity against parasitic, bacterial, fungal, and viral infections can be measured in vitro by measurement of inhibition of the TS of the infective agent, or by inhibition of the infective organism itself; and can be measured in vivo against animals infected with the infective organism.

The therapeutic ratio of a compound can be determined, for example, by comparing the dose that gives effective anti-tumor activity in a suitable in vivo model such as an L5178Y TK +/− tumor [see Fischer et al: Meth Med Res: 10: 247, 1964] in a suitable animal species such as the mouse, with the dose that gives significant weight loss (or other observable side-effects) in the test animal species. The therapeutic ratio of a compound for parasitic, bacterial, fungal, and viral infections can be measured in vitro by comparing the inhibition of the TS of the target infective organism and the inhibition of the TS of the animal in which the disease is to be treated, or may be determined in vitro by similar methods to those described previously for anti-tumor activity.

Pharmaceutical compositions and administration

In general, compounds of this invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. As anti-tumor agents, therapeutically effective amounts of compounds of this invention may range from 0.5 to 5000 milligrams per square meter ($mg/m^2$) body area of the animal, i.e. approximately 0.01–100 mg/Kg body weight; for example, 5–500 $mg/m^2$. A person of ordinary skill in the art will be able without undue experimentation, having regard to that skill and this disclosure, to determine a therapeutically effective amount of a compound of this invention for a given disease.

In general, compounds of this invention will be administered as pharmaceutical compositions by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

Typically, when administered as anti-tumor agents, compounds of this invention will be administered by intravenous injection. The amount of a compound of this invention in the composition may vary widely depending on the type of composition, size of a unit dosage, kind of excipients, and other factors well known to those of ordinary skill in the art. In general, the final composition may comprise from 0.000001 percent by weight (% w) to 10% w of the compound of this invention, preferably 0.00001% w to 1% w, with the remainder being the excipient or excipients.

An anti-tumor composition may optionally contain, in addition to a compound of this invention, at least one other compound of this invention, and/or at least one anti-tumor agent selected from, for example, mitotic inhibitors (e.g. vinblastine), alkylating agents (e.g. cisplatin, carboplatin, and cyclophosphamide), antimetabolites (e.g. 5-FU, cytarabine, and hydroxyurea), intercalating antibiotics (e.g. adriamycin), enzymes (e.g. asparaginase or PEG-asparaginase), topoisomerase inhibitors, and biological response modifiers.

When administered as anti-parasitic, anti-bacterial, anti-fungal, or anti-viral agents, compounds of this invention may be administered by any method and route of administration suitable to the treatment of the disease, typically as pharmaceutical compositions. As with the anti-tumor compositions mentioned previously, anti-parasitic, anti-bacterial, anti-fungal, or anti-viral compositions may optionally contain, in addition to a compound of this invention, at least one other compound of this invention and/or at least one other therapeutic agent useful in the treatment of the disease being treated.

Preparation of the Compounds of this Invention

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser's Reagents for Organic Synthesis, vols 1–17, John Wiley and Sons, New York, N.Y., 1991; Rodd's Chemistry of Carbon Compounds, vols. 1–5 and supps, Elsevier Science Publishers, 1989; Organic Reactions, vols 1–40, John Wiley and Sons, New York, N.Y., 1991; March J: Advanced Organic Chemistry, 4th ed. John Wiley and Sons, New York, N.Y., 1992; and Larock: Comprehensive Organic Transformations, VCH Publishers, 1989. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Unless specified to the contrary, the reactions described herein take place at atmospheric pressure over a temperature range between about 0° C. and 125° C.

The compounds of this invention may be prepared by the methods described below and as given in the Examples. Examples of ways in which modifications of the substituents on $R^2$ and $R^5$, in particular, may be made, be found in U.S. Pat. No. 4,992,550; U.S. Pat. No. 5,955,463; and Marsham P R, Wardleworth J M, Boyle F T, et al: Design and synthesis of potent non-polyglutamatable quinazoline antifolate thymidylate synthase inhibitors. J Med Chem: 42:3809–3820, 1999; all mentioned previously, and in references cited therein.

A general reaction scheme is shown below:

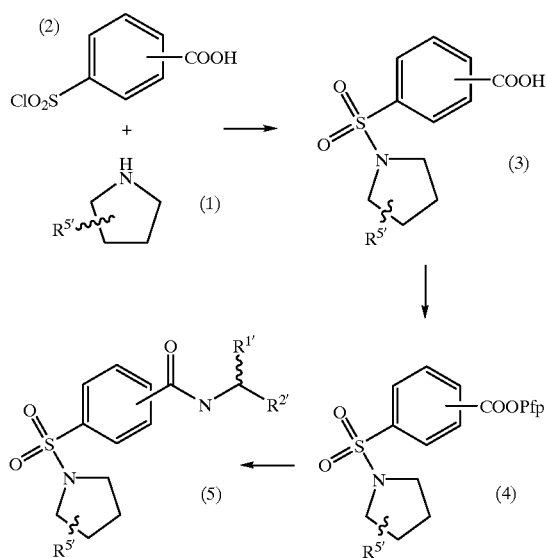

In this basic scheme, for clarity, the cyclic amine ring has been drawn as a pyrrolidine ring, and the possible X substituents on the benzene ring and the possible Y substituents on the pyrrolidine ring have been omitted, but no loss of generality is intended by these changes and omissions. It will be evident that the pyrrolidine ring may be replaced by a piperidine ring, and that non-interfering (or protected) substituents may be placed on these rings, without affecting the reactions shown.

In the first step, a carboxybenzenesulfonic acid chloride 2 is reacted with a (protected) $R^{5'}$-substituted pyrrolidine 1, such as proline methyl ester, in the presence of a weak base in water to form a carboxybenzenesulfonyl($R^{5'}$-substituted pyrrolidine) 3. This is then converted to an appropriate ester, such as the pentafluorophenyl (Pfp) ester 4 shown, by reaction with pentafluorophenyl trifluoroacetate and pyridine in DMF or a similar polar solvent, to activate the carbonyl group. Reaction with an amine of the formula $R^{1'}R^{2'}CHNH_2$, such as glutamic acid dimethyl ester, in the presence of an organic base such as triethylamine, in an organic solvent such as dichloromethane, gives a protected intermediate 5. The intermediate is then deprotected in one or more steps to give the final product of formula I (not shown in the scheme).

It will be evident that the proline methyl ester discussed can be replaced with an alternative ester of proline, or prolinamide, esters or amides of the phosphonic acid or sulfonic acid analogs of proline, the corresponding pipecolinic acid-based compounds, compounds where the proline is replaced by pyrrolidine-3-carboxylic acid or pipecolinic acid is replaced by piperidine-3-carboxylic acid or 4-carboxylic acid, or the 4-chlorosulfonylbenzoic acid is replaced by 3-chlorosulfonylbenzoic acid, and these compounds in which the pyrrolidine or piperidine ring and/or the benzene ring are substituted with substituents inert to the reaction conditions (or protected such substituents where the protecting group can be removed without adverse effect on the remainder of the compound). Similarly, the glutamic acid dimethyl ester discussed can be replaced with alternative esters of amino acids, aminophosphonic acids, aminosulfonic acids, dipeptides, substituted amino acids, and the like. Thus the choice of starting materials allows for the synthesis of a large variety of compounds of Formula I without further reaction.

This basic synthetic methodology is illustrated by Example 1.

When $R^{1'}$ or $R^{5'}$ is, for example, a carboxylic acid, sulfonic acid, or phosphonic acid, it will typically be protected throughout the synthesis as an alkyl, e.g. $C_{1-4}$ alkyl ester, typically the methyl ester; with the ester being removed in the final deprotection step by reaction with an aqueous base, such as aqueous lithium hydroxide. When $R^{1'}$ or $R^{5'}$ is, for example, a carboxamide or sulfonamide, it will typically be protected with a typical amine-protecting group well known to a person of ordinary skill in the art, such as tert-butoxycarbonyl (BOC), benzyloxycarbonyl (CBZ), 9-fluorenylmethoxycarbonyl (FMOC), and the like, if needed, with the protecting group being removed in the final deprotection step by such methods as are conventional for removal of these amine-protecting groups. Thus deprotection of these $R^{1'}$ and $R^{5'}$ groups will lead to compounds where the substituents $R^1$ and $R^5$ are —COOH, —CONH$_2$, —SO$_3$H, —SO$_2$NH$_2$, or —PO$_3$H$_2$.

Similarly, when the substituent on $R^2$ of formula I is to be —COOH, —CONH$_2$, —SO$_3$H, —SO$_2$NH$_2$, or —PO$_3$H$_2$, then the substituent on $R^{2'}$ will be protected as described immediately above for $R^{1'}$ or $R^{5'}$, and will be deprotected in the same manner in the final deprotection step(s).

When $R^5$ is to be —CONHR$^2$ or —SO$_2$NHR$^2$, then $R^{5'}$ should be a carboxylic acid or sulfonic acid protected as an ester that is differentially removable, i.e. removable under circumstances where other carboxyl or sulfonyl groups remain protected. For example, if the proline methyl ester is replaced by proline tert-butyl ester and the appropriate intermediate of formula 5 formed, then the tert-butyl ester may be selectively removed while methyl groups remain on the carboxylates of $R^{1'}$ and $R^{2'}$. This removal may be carried out, for example, by reaction of the compound of formula 5 with 50% trifluoroacetic acid in dichloromethane, with triethylsilane as a scavenger. The free terminal acidic group may then be converted to the pentafluorophenyl ester for activation, and reacted with an appropriate amine of the formula $R^{2'}NH_2$ to form a new intermediate of formula 5, which can then be deprotected in the same manner as described previously.

This modified synthetic methodology is illustrated by Example 2.

If the substituent on $R^2$ is to be —CONHR$^3$, —CONHCOR$^4$, —CONHSO$_2$R$^4$, —SO$_2$NHR$^3$, —SO$_2$NHCOR$^4$, or —SO$_2$NHSO$_2$R$^4$; then the original $R^{2'}$ will contain a carboxyl or sulfonyl group protected as an ester that is differentially removable. Then $R^2$ may be extended in the same manner as described above for the "extension" of $R^5$ through a carboxamide or sulfonamide linkage, by reaction with a (protected) amine $R^{3'}NH_2$, amide $R^{4'}CONH_2$, or sulfonamide $R^{4'}SO_2NH_2$, where $R^{3'}$ denotes $R^3$ protected where necessary to enable the reaction to produce the desired product. Alternatively, a carboxyl substituent, exposed by appropriate deprotection, can be converted into an aminosulfonylmethyl group by reduction to the alcohol (reaction with ethyl chloroformate and triethylamine followed by reduction with sodium borohydride), conversion to the mesylate and esterification with thioacetic acid, conversion to the methylsulfonyl chloride, then to the methylsulfonamide, and, by reaction with $R^4COCl$ or $R^4SO_2Cl$, into a substituent of formula —SO$_2$NHCOR$^4$ or —SO$_2$NHSO$_2$R$^4$, by methods analogous to those described in, and illustrated in Scheme 2 of, Marsham et al.

If the substituent on $R^2$ is to be -4-triazolyl, -5-tetrazolyl, or -5-(3-oxo-1,2,4-triazolyl), desirably the appropriate amine $R^{1'}R^{2'}CHNH_2$, will first be purchased or synthesized, such as by the method of Van T T, Kojiro E, Grzonka Z: Synthesis of γ-tetrazole analogs of glutamic acid and its derivatives. Tetrahedron 33:2299–2302, 1977, or by other methods known to a person of ordinary skill in the art, and then coupled to the pentafluorophenyl benzoate intermediate of formula 4, and further reacted or deprotected as appropriate to the compound of formula I to be prepared.

If the substituent on $R^2$ is to be —$S(O)_m$-4-triazolyl, —$S(O)_m$-5-tetrazolyl, or —$S(O)_m$-5-(3-oxo-1,2,4-triazolyl), then the appropriate amine $R^{1'}R^{2'}CHNH_2$ containing a triazolylthio, etc., substituent will be prepared from a hydroxyamine, via the mesylate, by reaction with the sodium salt of triazolethiol, tetrazolethiol, or oxotriazolylthiol. The amine is then coupled to the pentafluorophenyl benzoate intermediate of formula 4, oxidized (for example, with peracetic acid in chloroform/methanol), and further reacted or deprotected as appropriate to the compound of formula I to be prepared. These methods are described in, and illustrated in Scheme 3 of, Marsham et al.

Generally, if the side chain $R^1R^2CH$— is complex, it will be preferable to assemble the appropriate amine first, in protected form as necessary, and then couple it to the pentafluorophenyl benzoate intermediate of formula 4, rather than assemble the side chain after formation of the benzamide bond. In particular, dipeptides and esterified dipeptides, such as glutamylglutamic acid, are readily available. However, a person of ordinary skill in the art, having regard to that skill, this disclosure, and the references cited herein, will be able to prepare desired compounds of formula I without undue experimentation.

EXAMPLES

The following non-limiting examples illustrate the invention. All commercially available materials were used as received. All synthesized compounds were characterized by $^1H$ NMR (Bruker DMX 400 MHz Spectrometer) and high-performance liquid-chromatography/mass-spectroscopy (HPLC-MS, Hewlett-Packard Series 1100 MSD), and judged to be at least 95% pure before testing in enzymatic assays.

Example 1
2-[4-(2(R)-Carboxypyrrolidine-1-sulfonyl)benzoylamino]pentane-(S)-dioic acid

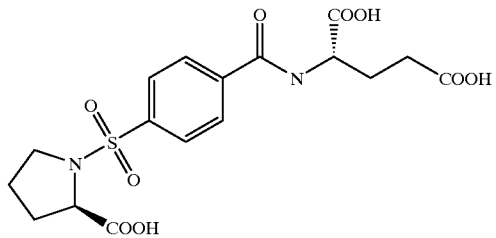

Step A. 1-(R)-(4-Carboxybenzenesulfonyl)pyrrolidine-2-carboxylic acid methyl ester To (R)-pyrrolidine-2-carboxylic acid methyl ester hydrochloride (D-Pro-OMe.HCl) (1.0 g, 6.04 mmol) was added 4-chlorosulfonylbenzoic acid (1.32 g, 6 mmol) and sodium carbonate (2.0 g, 18.5 mmol). The solids were dissolved in 40 mL water and stirred for 14 hours at ambient temperature. The solution was then acidified with 50 mL 1M aqueous sodium hydrogen sulfate and extracted with ethyl acetate (1×50 mL, 3×20 mL). The combined organic extracts were rinsed with 50 mL 5M aqueous sodium chloride, dried over anhydrous sodium sulfate, filtered, and evaporated to dryness to produce 1-(R)-(4-carboxybenzenesulfonyl)pyrrolidine-2-carboxylic acid methyl ester as a white solid, weighing 1.62 g (5.19 mmol, 86%).

Step B. 1-(R)-(4-Pentafluorophenyloxycarbonylbenzenesulfonyl)pyrrolidine-2-carboxylic acid methyl ester The product from the previous step was dissolved in 7 mL dry N,N-dimethylformamide (DMF. To this was added pyridine (0.63 mL, 7.79 mmol) and pentafluorophenyl trifluoroacetate (1.34 mL, 7.80 mmol). The reaction was stirred at ambient temperature for 3.5 hours before diluting with ethyl acetate (100 mL). This was then rinsed with 50 mL 1M aqueous sodium carbonate, 50 mL 1M aqueous sodium hydrogen sulfate, and 50 mL 5M aqueous sodium chloride. The solvent was removed by rotary evaporation, and the residue redissolved in a few milliliters of chloroform and purified by flash chromatography (4 cm column, 80:20 hexane:ethyl acetate, switching to 60:40 hexane:ethyl acetate). Fractions containing the pure product were combined and evaporated to dryness, yielding a white crust of 1-(R)-(4-pentafluorophenyloxycarbonylbenzenesulfonyl)pyrrolidine-2-carboxylic acid methyl ester weighing 2.11 g (4.41 mmol, 73% from pyrrolidine-2-carboxylic acid methyl ester).

Step C. 2-[4-(2(R)-Methoxycarbonylpyrrolidine-1-sulfonyl)benzoylamino]pentane-(S)-dioic acid dimethyl ester To the product from the previous step (0.4 g, 0.835 mmol) was added (S)-glutamic acid dimethyl ester hydrochloride (0.18 g). These were dissolved in 5 mL dry dichloromethane, and triethylamine (0.47 mL, 3.37 mmol) was added. The reaction was allowed to proceed for 15 hours at ambient temperature, at which time it was flooded with 100 mL ethyl acetate, rinsed with 50 mL 1M aqueous sodium hydrogen sulfate, 50 mL 1M aqueous sodium carbonate, and 50 mL 5M aqueous sodium chloride. The solvent was removed by rotary evaporation and the residue purified by flash chromatography (2 cm silica gel column, 70:30 chloroform:ethyl acetate). The purified 2-[4-(2(R)-methoxycarbonylpyrrolidine-1-sulfonyl)benzoylamino]pentane-(S)-dioic acid dimethyl ester product weighed 0.322 g (0.685 mmol, 82%).

Step D. 2-[4-(2(R)-Carboxypyrrolidine-1-sulfonyl)benzoylamino]pentane-(S)-dioic acid To the product from the previous step was added lithium hydroxide (66 mg, 2.76 mmol) and 15 mL water. The reaction was stirred vigorously at ambient temperature for 3.5 hours. The solution was acidified with 3 mL 1M aqueous hydrochloric acid, flash-frozen, and lyophilized. The dry white crust was then redissolved in 4.5 mL water and 1.5 mL acetonitrile and purified by reverse phase chromatography to yield 2-[4-(2(R)-carboxypyrrolidine-1-sulfonyl)benzoylamino]pentane-(S)-dioic acid (110 mg, 0.258 mmol, 38%), MS: calc. 428, obs. 429 (M+H).

In a similar manner using L-proline methlyl ester, DL-proline methyl ester, and DL-pipecolinic acid methyl ester in place of D-proline methyl ester, there were prepared 2-[4-(2(S)-carboxypyrrolidine-1-sulfonyl)benzoylamino]pentane-(S)-dioic acid, MS: calc. 428, obs. 429 (M+H), 2-[4-(2(RS)-carboxypyrrolidine-1-sulfonyl)benzoylamino]pentane-(S)-dioic acid, MS: calc. 428, obs. 429 (M+H), and 2-[4-(2(RS)-carboxypiperidine-1-sulfonyl)benzoylamino]pentane-(S)-dioic acid, MS: calc. 442, obs. 443 (M+H), respectively.

In a similar manner using the dimethyl esters of (S)-aspartic acid, (S)-2-aminohexanoic acid, (R)-2- aminoheptanoic acid, (R)-2-aminooctanoic acid, (RS)-2-aminooctanoic acid, and the methyl ester of (S)-glutamine in place of (S)-glutamic acid dimethyl ester, there were obtained 2-[4-(2(R)-carboxypyrrolidine-1-sulfonyl)benzoylamino]butane-(S)-dioic acid, MS: calc. 414, obs. 415 (M+H), 2-[4-(2(R)-carboxypyrrolidine-1-sulfonyl)benzoylamino]hexane-(S)-dioic acid, MS: calc. 442, obs. 443 (M+H), 2-[4-(2(R)-carboxypyrrolidine-1-sulfonyl)benzoylamino]heptane-(S)-dioic acid, MS: calc. 456, obs. 457 (M+H), 2-[4-(2(R)-carboxypyrrolidine-1-sulfonyl)benzoylamino]octane-(R)-dioic acid, MS: calc. 470, obs. 471 (M+H), 2-[4-(2(R)-carboxypyrrolidine-1-sulfonyl)benzoylamino]octane-(RS)-dioic acid, MS: calc. 470, obs. 471 (M+H), and 4-aminocarbonyl-2-[4-(2(R)-carboxypyrrolidine-1-sulfonyl)benzoylamino]-(S)-butanoic acid, MS: calc. 427, obs. 428 (M+H).

Example 2

2-{4-[2(R)-(2-Carboxyethylaminocarbonyl)pyrrolidine-1-sulfonyl]benzoylamino}-pentane-(S)-dioic acid

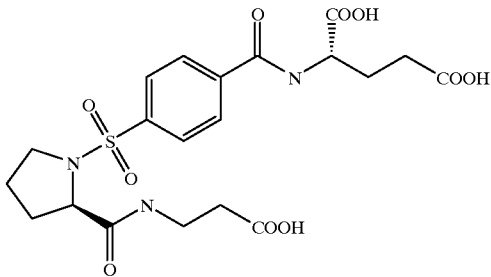

Step A. 1-(R)-(4-Carboxybenzenesulfonyl)pyrrolidine-2-carboxylic acid tert-butyl ester To 4-chlorosulfonylbenzoic acid (1.29 g) in 10 mL dry DMF and 10 mL dry tetrahydrofuran (TIF) was added (R)-pyrrolidine-2-carboxylic acid tert-butyl ester (D-Pro-OtBu), (1 g, 5.84 mmol) and pyridine (1.2 mL, 14.8 mmol). This was done in an ice-water bath, which was slowly allowed to warm to ambient temperature. After 13 hours, pyridine (0.71 mL, 8.78 mmol) and pentafluorophenyl trifluoroacetate (1.51 mL, 8.79 mmol) were added. The reaction was allowed to proceed at ambient temperature for 1.25 hours, flooded with 100 mL ethyl acetate, rinsed with 50 mL 1M aqueous sodium carbonate, 50 mL 1M aqueous sodium hydrogen sulfate, and 50 mL 5M aqueous sodium chloride, dried over anhydrous sodium sulfate, filtered, and evaporated to dryness.

Step B. 2-[4-(2(R)-tert-Butoxycarbonylpyrrolidine-1-sulfonyl)benzoylamino]pentane-(S)-dioic acid dimethyl ester The crude product from the previous step was mixed with (S)-glutamic acid dimethyl ester hydrochloride (1.9 g, 8.8 mmol) and dissolved in 20 mL dichloromethane, followed by addition of triethylamine (4.9 mL, 35 mmol). After 5 hours at ambient temperature the reaction was flooded with 100 mL ethyl acetate, rinsed with 2×50 mL 1M aqueous sodium hydrogen sulfate and 50 mL 5M aqueous sodium chloride, dried over anhydrous sodium sulfate, filtered, and evaporated to dryness. The residue was purified by flash chromatography (4 cm silica gel column, 70:30 chloroform:ethyl acetate). The product has an $R_f$ of 0.26 in this solvent system. After chromatography the product is evaporated to dryness yielding 1.25 g (2.45 mmol, 42% from pyrrolidine-2-carboxylic acid tert-butyl ester)

Step C. 2-[4-(2(R)-Pentafluorophenyloxycarbonylpyrrolidine-1-sulfonyl)benzoylamino]pentane-(S)-dioic acid dimethyl ester The product from the previous step was dissolved in 25 mL dry dichloromethane. To this was added triethylsilane (2.9 mL, 18.2 mmol) and 25 mL neat trifluoroacetic acid. The reaction was allowed to stir at ambient temperature for 45 minutes, after which time it was evaporated to dryness and submitted to high vacuum overnight. The residue was then dissolved in 5 mL dry DMF and reacted with pyridine (0.4 mL, 4.95 mmol) and pentafluorophenyl trifluoroacetate (0.84 mL, 4.89 mmol). This was allowed to stir for 3 hours at ambient temperature, at which point the reaction was flooded with 100 mL ethyl acetate, rinsed with 50 mL 1M aqueous sodium carbonate, 50 mL 1M aqueous sodium hydrogen sulfate, 50 mL 5M aqueous sodium chloride, evaporated to dryness, and purified by flash chromatography (4 cm column, 70:30 chloroform:ethyl acetate). Fractions containing pure product were combined and evaporated to dryness to yield 1.07 g (1.73 mmol, 70% for two steps).

Step D. 2-{4-[2(R)-(2-Carboxyethylaminocarbonyl)-pyrrolidine-1-sulfonyl]-benzoylamino}-pentane(S)dioic acid To the product from the previous step (221 mg, 0.355 mmol) was added 3-aminopropionic acid methyl ester hydrochloride (82 mg, 0.534 mmol), 5 mL dry dichloromethane, and triethylamine (0.2 mL, 1.43 mmol). The reaction was allowed to stir at ambient temperature for 1.5 hours, after which point it was flooded with 100 mL ethyl acetate. The combined organic layer was rinsed with 50 mL 1M aqueous sodium carbonate, 50 mL 1M aqueous sodium hydrogen sulfate, and 50 mL 5M aqueous sodium chloride, dried over anhydrous sodium sulfate, filtered, and evaporated to dryness. To this was added lithium hydroxide (34 mg, 1.42 mmol) and 5 mL water, and the reaction mixture was stirred at ambient temperature for two hours. The reaction was acidified with 1.5 mL 1N aqueous hydrochloric acid, filtered, and purified by reverse phase HPLC to yield 2-{4-[2(R)-(2-carboxyethylaminocarbonyl)-pyrrolidine-1-sulfonyl]benzoylamino}pentane-(S)-dioic acid (81 mg, 0.162 mmol, 36% for two steps), MS: calc. 499, obs. 500 (M+H).

In a similar manner, substituting the methyl esters of glycine, 4-aminobutanoic acid, and 6-aminohexanoic acid for 3-aminopropionic acid methyl ester, there were obtained 2-{4-[2(R)-(carboxymethylaminocarbonyl)-pyrrolidine-1-sulfonyl]benzoylamino}pentane-(S)-dioic acid, MS: calc. 485, obs. 486 (M+H), 2-{4-[2(R)-(3-carboxypropylaminocarbonyl)-pyrrolidine-1-sulfonyl]benzoylamino}pentane-(S)-dioic acid, MS: calc. 513, obs. 514 (M+H), and 2-{4-[2(R)-(5-carboxypentylaminocarbonyl)-pyrrolidine-1-sulfonyl]benzoylamino}pentane-(S)-dioic acid, MS: calc. 541, obs. 542 (M+H), respectively.

Example 3

Inhibition of Thymidylate Synthase

TS was expressed, purified, and characterized by SDS-PAGE and mass spectroscopy. Enzymatic inhibition assays were performed by the methods described in Wahba A J and Friedkin M: Direct spectrophotometric evidence for the oxidation of tetrahydrofolate during the enzymatic synthesis of thymidylate. J Biol Chem: 236: PCI11–PC12, 1961; and Chen S C, Daron H H, and Aull J L: Inhibition of thymidylate synthase by pyridoxal phosphate. Int J Biochem: 21: 1217–1221, 1989, mentioned previously.

Briefly, the assay buffer consisted of 50 mM TES pH 7.4; 71 mM 2-mercaptoethanol, 15 mM formaldehyde, 25 mM magnesium chloride, and 0.04 mM 6R-methylenetetrahydrofolate. The compound to be tested (dissolved in dimethylsulfoxide) was added to 0.5 mL of this solution such that the final concentration of DMSO was never higher than 3% v/v. 2'-deoxyuridinemonophosphate (dUMP) was added; and finally TS (5 μL) was added, the solution mixed rapidly, and the reaction followed at 340 nm (with background correction) in a UV-vis spectrophotometer. Inhibition constants were calculated as described by Chen et al. Compounds of the invention demonstrated inhibition of TS in this assay, and were competitive with respect to dUMP.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. A compound of formula I:

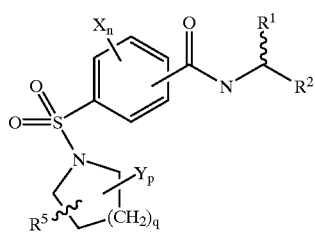

(I)

where:

$R^1$ is —COOH, —CONH$_2$, —SO$_3$H, —SO$_2$NH$_2$, —PO$_3$H$_2$;

$R^2$ is C$_{1-6}$ alkyl optionally substituted with —COOH, —CONH$_2$, —CONHR$^3$, —CONHCOR$^4$, —CONHSO$_2$R$^4$, —SO$_3$H, —SO$_2$NH$_2$, —SO$_2$NHR$^3$, —SO$_2$NHCOR$^4$, —SO$_2$NHSO$_2$R$^4$, —PO$_3$H$_2$, -4-(1,2,3-triazolyl), -5-tetrazolyl, -5-(3-oxo-1,2,4-triazolyl), —S(O)$_m$-4-(1,2,3-triazolyl), —S(O)$_m$-5-tetrazolyl, or —S(O)$_m$-5-(3-oxo-1,2,4-triazolyl);

$R^3$ is a group such that $R^3$—NH$_2$ is an amino acid;

$R^4$ is C$_{1-4}$ alkyl, trifluoromethyl, or phenyl optionally substituted with methyl, trifluoromethyl, or nitro;

m is 0, 1, or 2;

each X and Y, which may be the same or different, is independently selected from methyl, ethyl, isopropyl, ethenyl, ethynyl, fluoro, chloro, bromo, methylthio, hydroxy, methoxy, carboxy, and methoxycarbonyl;

n is 0, 1, 2, or 3;

p is 0, 1, or 2;

q is 1 or 2;

$R^5$ is —COOH, —CONH$_2$, —CONHR$^2$, —SO$_3$H, —SO$_2$NH$_2$, —SO$_2$NHR$^2$, or —PO$_3$H$_2$, as an individual stereoisomer or mixture of stereoisomers, or a pharmaceutically acceptable salt or ester thereof.

2. A compound of claim 1 where $R^1$ is —COOH; $R^2$ is C$_{2-6}$ alkyl ω-substituted with —COOH, —CONH$_2$, —CONHR$^3$, —SO$_2$NH$_2$, or —SO$_2$NHR$^3$, -4-triazolyl, or -5-tetrazolyl; $R^3$ is an acidic amino acid; each X and Y is independently methyl, ethyl, fluoro, chloro, bromo, methoxy, carboxy, or methoxycarbonyl; n and p are independently 0 or 1; and $R^5$ is —CONHR$^{2'}$ where $R^{2'}$ is C$_{2-6}$ alkyl ω-substituted with —COOH, —CONH$_2$, —SO$_3$H, —SO$_2$NH$_2$, -4-triazolyl, or -5-tetrazolyl, as an individual stereoisomer or mixture of stereoisomers, or a pharmaceutically acceptable salt or ester thereof.

3. A compound of claim 1 where $R^1$ is —COOH; $R^2$ is C$_{2-6}$ alkyl ω-substituted with —CONHR$^3$ or —SO$_2$NHR$^3$; $R^3$ is an acidic amino acid; each X and Y is independently methyl, ethyl, fluoro, chloro, bromo, or methoxy; n and p are independently 0 or 1; and $R^5$ is —CORNHR$^{2'}$ where $R^{2'}$ is C$_{2-6}$ alkyl ω-substituted with —COOH, —CONH$_2$, -4-trazolyl, or -5-tetrazolyl, as an individual stereoisomer or mixture of stereoisomers, or a pharmaceutically acceptable salt or ester thereof.

4. A compound of claim 1 where $R^1$ is —COOH; $R^2$ is C$_{2-6}$ alkyl ω-substituted with —CONHR$^3$; $R^3$ is an acidic amino acid selected from glutamic acid, 2-aminohexanedioic acid, 2-aminoheptanedioic acid, or 2-aminooctanedioic acid; n and p are 0; and $R^5$ is —CONHR$^{2'}$ where $R^{2'}$ is C$_{2-6}$ alkyl ω-substituted with —COOH or —CONH$_2$, as an individual stereoisomer or mixture of stereoisomers, or a pharmaceutically acceptable salt or ester thereof.

5. A compound of claim 1 where $R^1$ is —COOH; $R^2$ is C$_{2-6}$ alkyl ω-substituted with —COOH; n and p are 0; and $R^5$ is —CONHR$^{2'}$ where $R^{2'}$ is C$_{2-6}$ alkyl ω-substituted with —COOH or —CONH$_2$, as an individual stereoisomer or mixture of stereoisomers, or a pharmaceutically acceptable salt or ester thereof.

6. A compound of claim 1 that is:

2-[4-(2-carboxypyrrolidine-1-sulfonyl)benzoylamino]octanedioic acid;

2-[4-(2-carboxypyrrolidine-1-sulfonyl)benzoylamino]-4-[1,3-dicarboxypropylaminocarbonyl]butanoic acid;

2-[4-(2-carboxypiperidine-1-sulfonyl)benzoylamino]-4-[1,3-dicarboxypropylaminocarbonyl]butanoic acid;

2-{4-[2-(2-carboxyethylaminocarbonyl)pyrrolidine-1-sulfonyl]benzoylamino}pentanedioic acid;

2-{4-[2-(3-carboxypropylaminocarbonyl)-pyrrolidine-1-sulfonyl]benzoylamino}pentanedioic acid;

2-{4-[2-(5-carboxypentylaminocarbonyl)-pyrrolidine-1-sulfonyl]benzoylamino}pentanedioic acid; or 2-{4-[2-(3-methylbutylaminocarbonyl)-pyrrolidine-1-sulfonyl]benzoylamino}pentanedioic acid; as an individual stereoisomer or mixture of stereoisomers, or a pharmaceutically acceptable salt or ester thereof.

7. A pharmaceutical composition comprising:

(a) a therapeutically effective amount of a compound of claim 1; and (b) a pharmaceutically acceptable excipient.

8. A pharmaceutical composition comprising:

(a) a therapeutically effective amount of a compound of claim 2; and (b) a pharmaceutically acceptable excipient.

9. A pharmaceutical composition comprising:

(a) a therapeutically effective amount of a compound of claim 3; and (b) a pharmaceutically acceptable excipient.

10. A pharmaceutical composition comprising:

(a) a therapeutically effective amount of a compound of claim 4; and (b) a pharmaceutically acceptable excipient.

11. A pharmaceutical composition comprising:

(a) a therapeutically effective amount of a compound of claim 5; and (b) a pharmaceutically acceptable excipient.

12. A pharmaceutical composition comprising:
(a) a therapeutically effective amount of a compound of claim 6; and
(b) a pharmaceutically acceptable excipient.

13. A method of treating an animal having a disease capable of treatment by administration of a thymidylate synthase inhibitor, comprising administration to that animal of a therapeutically effective amount of a compound of claim 1.

14. A method of treating an animal having a disease capable of treatment by administration of a thymidylate synthase inhibitor, comprising administration to that animal of a therapeutically effective amount of a compound of claim 2.

15. A method of treating an animal having a disease capable of treatment by administration of a thymidylate synthase inhibitor, comprising administration to that animal of a therapeutically effective amount of a compound of claim 3.

16. A method of treating an animal having a disease capable of treatment by administration of a thymidylate synthase inhibitor, comprising administration to that animal of a therapeutically effective amount of a compound of claim 4.

17. A method of treating an animal having a disease capable of treatment by administration of a thymidylate synthase inhibitor, comprising administration to that animal of a therapeutically effective amount of a compound of claim 5.

18. A method of treating an animal having a disease capable of treatment by administration of a thymidylate synthase inhibitor, comprising administration to that animal of a therapeutically effective amount of a compound of claim 6.

19. A method of claim 13 where the disease is cancer.

20. A method of claim 13 where the disease is a parasitic, bacterial, fungal, or viral infection.

\* \* \* \* \*

UNITED STATES PATENT AND TRADEMARK OFFICE
CERTIFICATE OF CORRECTION

PATENT NO.   : 6,143,776
DATED        : November 7, 2000
INVENTOR(S)  : Daniel A. Erlanson Page 1 of 1

It is certified that error appears in the above-identified patent and that said Letters Patent is hereby corrected as shown below:

Column 1,
Line 4, insert the following paragraph: -- This invention was made with Government Support under SBIR Grant No. R43 CA85141 awarded by the Public Health Service. The Government has certain rights in the invention. --

Signed and Sealed this

Twenty-first Day of May, 2002

*Attest:*

JAMES E. ROGAN
*Director of the United States Patent and Trademark Office*

*Attesting Officer*